(12) United States Patent
Johnson et al.

(10) Patent No.: US 9,968,378 B1
(45) Date of Patent: May 15, 2018

(54) ADAPTATION SPHERE SADDLE

(71) Applicants: Wesley M. Johnson, Tampa, FL (US); Thomas B. Freeman, Tampa, FL (US)

(72) Inventors: Wesley M. Johnson, Tampa, FL (US); Thomas B. Freeman, Tampa, FL (US)

(73) Assignee: University of South Florida, Tampa, FL (US)

( * ) Notice: Subject to any disclaimer, the term of this patent is extended or adjusted under 35 U.S.C. 154(b) by 12 days.

(21) Appl. No.: 15/199,053

(22) Filed: Jun. 30, 2016

Related U.S. Application Data

(60) Provisional application No. 62/195,584, filed on Jul. 22, 2015.

(51) Int. Cl.
*A61B 17/70* (2006.01)

(52) U.S. Cl.
CPC ...... *A61B 17/7037* (2013.01); *A61B 17/7002* (2013.01); *A61B 17/7032* (2013.01)

(58) Field of Classification Search
CPC .................................... A61B 17/7035–17/704
See application file for complete search history.

(56) References Cited

U.S. PATENT DOCUMENTS

| 5,520,690 | A | 5/1996 | Errico et al. | |
|---|---|---|---|---|
| 5,882,350 | A | 3/1999 | Ralph et al. | |
| 6,565,569 | B1 * | 5/2003 | Assaker | A61B 17/7037 606/250 |
| 6,896,677 | B1 * | 5/2005 | Lin | A61B 17/7032 606/266 |
| 7,211,086 | B2 * | 5/2007 | Biedermann | A61B 17/7032 606/308 |
| 7,291,153 | B2 * | 11/2007 | Glascott | A61B 17/7032 606/308 |
| 8,236,035 | B1 * | 8/2012 | Bedor | A61B 17/7037 606/266 |
| 8,277,490 | B2 | 10/2012 | Freeman et al. | |
| 8,858,605 | B1 * | 10/2014 | Glatzer | A61B 17/7037 606/266 |
| 8,906,068 | B1 * | 12/2014 | Bedor | A61B 17/7037 606/267 |
| 8,926,669 | B2 * | 1/2015 | Jacofsky | A61B 17/7032 606/264 |

(Continued)

FOREIGN PATENT DOCUMENTS

WO  2007035884 A2  3/2007

*Primary Examiner* — Eduardo C Robert
*Assistant Examiner* — Michelle C Eckman
(74) *Attorney, Agent, or Firm* — Andriy Lytvyn; Smith & Hopen, P.A.

(57) ABSTRACT

An improvement of a polyaxial screw head disclosed in the U.S. Pat. No. 8,277,490. A saddle resides within a tulip. The saddle is configured to mate with a rod. An outer set screw engages an inner surface of the tulip. An inner set screw is disposed within a lumen of an outer set screw. A force distributor has a concave surface configured to mate with the rod. The force distributor has a bore configured to accept a conical end of the inner set screw. The force distributor is configured to distribute the force applied onto the bore by the inner set screw along the contact area with rod. The force distributor allows the rod to pivot and have sagittal motion when the inner set screw is untightened. The force distributor immobilizes the rod within the saddle when the inner set screw is tightened.

16 Claims, 2 Drawing Sheets

(56) References Cited

U.S. PATENT DOCUMENTS

| | | | |
|---|---|---|---|
| 9,345,519 B1 * | 5/2016 | Poirier | A61B 17/7032 |
| 9,622,788 B2 * | 4/2017 | Rezach | A61B 17/7037 |
| 9,655,655 B2 * | 5/2017 | Haskins | A61B 17/7035 |
| 2001/0001119 A1 * | 5/2001 | Lombardo | A61B 17/7037 |
| | | | 606/264 |
| 2002/0082601 A1 * | 6/2002 | Toyama | A61B 17/7032 |
| | | | 606/308 |
| 2003/0078580 A1 * | 4/2003 | Shitoto | A61B 17/7035 |
| | | | 606/264 |
| 2003/0109882 A1 * | 6/2003 | Shirado | A61B 17/7032 |
| | | | 606/324 |
| 2004/0153070 A1 * | 8/2004 | Barker | A61B 17/7044 |
| | | | 606/281 |
| 2004/0254577 A1 * | 12/2004 | Delecrin | A61B 17/7007 |
| | | | 606/261 |
| 2004/0260283 A1 * | 12/2004 | Wu | A61B 17/7032 |
| | | | 606/270 |
| 2005/0131409 A1 * | 6/2005 | Chervitz | A61F 2/30771 |
| | | | 606/247 |
| 2005/0187548 A1 | 8/2005 | Butler et al. | |
| 2005/0192571 A1 | 9/2005 | Abdelgany | |
| 2005/0234452 A1 * | 10/2005 | Malandain | A61B 17/7007 |
| | | | 606/54 |
| 2005/0261687 A1 * | 11/2005 | Garamszegi | A61B 17/7011 |
| | | | 606/305 |
| 2005/0277919 A1 * | 12/2005 | Slivka | A61B 17/7032 |
| | | | 606/256 |
| 2005/0277924 A1 * | 12/2005 | Roychowdhury | A61B 17/7032 |
| | | | 606/308 |
| 2006/0079895 A1 * | 4/2006 | McLeer | A61B 17/863 |
| | | | 606/279 |
| 2006/0116677 A1 * | 6/2006 | Burd | A61B 17/7032 |
| | | | 74/1 R |
| 2006/0149234 A1 * | 7/2006 | de Coninck | A61B 17/7035 |
| | | | 606/278 |
| 2006/0149235 A1 * | 7/2006 | Jackson | A61B 17/7032 |
| | | | 606/328 |
| 2006/0200131 A1 | 9/2006 | Chao et al. | |
| 2006/0229615 A1 * | 10/2006 | Abdou | A61B 17/8685 |
| | | | 606/256 |
| 2006/0241600 A1 | 10/2006 | Ensign et al. | |
| 2006/0264933 A1 | 11/2006 | Baker et al. | |
| 2006/0271193 A1 * | 11/2006 | Hartmann | A61B 17/7032 |
| | | | 623/17.11 |
| 2006/0276792 A1 | 12/2006 | Ensign et al. | |
| 2007/0043358 A1 * | 2/2007 | Molz, IV | A61B 17/7037 |
| | | | 623/17.16 |
| 2007/0118118 A1 * | 5/2007 | Kwak | A61B 17/7032 |
| | | | 606/279 |
| 2007/0161999 A1 * | 7/2007 | Biedermann | A61B 17/7037 |
| | | | 606/254 |
| 2007/0270813 A1 * | 11/2007 | Garamszegi | A61B 17/7032 |
| | | | 606/278 |
| 2008/0045953 A1 * | 2/2008 | Garamszegi | A61B 17/7032 |
| | | | 606/86 A |
| 2008/0086132 A1 * | 4/2008 | Biedermann | A61B 17/7037 |
| | | | 606/279 |
| 2008/0114362 A1 * | 5/2008 | Justis | A61B 17/7002 |
| | | | 606/267 |
| 2008/0195159 A1 * | 8/2008 | Kloss | A61B 17/7037 |
| | | | 606/305 |
| 2008/0234757 A1 * | 9/2008 | Jacofsky | A61B 17/7032 |
| | | | 606/308 |
| 2009/0012565 A1 * | 1/2009 | Sachs | A61B 17/7041 |
| | | | 606/246 |
| 2009/0062866 A1 * | 3/2009 | Jackson | A61B 17/7032 |
| | | | 606/301 |
| 2009/0198280 A1 * | 8/2009 | Spratt | A61B 17/7037 |
| | | | 606/267 |
| 2009/0210015 A1 * | 8/2009 | Cermak | A61B 17/7037 |
| | | | 606/305 |
| 2009/0216280 A1 * | 8/2009 | Hutchinson | A61B 17/88 |
| | | | 606/279 |
| 2010/0152776 A1 * | 6/2010 | Keyer | A61B 17/7031 |
| | | | 606/257 |
| 2011/0066187 A1 * | 3/2011 | Fang | A61B 17/7002 |
| | | | 606/254 |
| 2011/0106173 A1 * | 5/2011 | Lindemann | A61B 17/7037 |
| | | | 606/302 |
| 2011/0106174 A1 * | 5/2011 | Rezach | A61B 17/7032 |
| | | | 606/305 |
| 2011/0106180 A1 * | 5/2011 | Miller | A61B 17/7032 |
| | | | 606/308 |
| 2011/0144694 A1 * | 6/2011 | Laeng | A61B 17/7037 |
| | | | 606/263 |
| 2011/0257690 A1 * | 10/2011 | Rezach | A61B 17/7037 |
| | | | 606/302 |
| 2012/0143260 A1 * | 6/2012 | Gunn | A61B 17/7032 |
| | | | 606/302 |
| 2013/0103093 A1 * | 4/2013 | Biedermann | A61B 17/7035 |
| | | | 606/272 |
| 2013/0150904 A1 * | 6/2013 | Biedermann | A61B 17/84 |
| | | | 606/328 |
| 2013/0172937 A1 * | 7/2013 | Davenport | A61B 17/7032 |
| | | | 606/278 |
| 2014/0081334 A1 * | 3/2014 | Jackson | A61B 17/7035 |
| | | | 606/278 |
| 2014/0094849 A1 * | 4/2014 | Spratt | A61B 17/7035 |
| | | | 606/257 |
| 2014/0142632 A1 * | 5/2014 | Keyer | A61B 17/7037 |
| | | | 606/265 |
| 2014/0142633 A1 * | 5/2014 | Jackson | A61B 17/7032 |
| | | | 606/273 |
| 2014/0236235 A1 * | 8/2014 | Jackson | A61B 17/7037 |
| | | | 606/267 |
| 2014/0277153 A1 * | 9/2014 | Spratt | A61B 17/7035 |
| | | | 606/266 |
| 2014/0277159 A1 * | 9/2014 | Spratt | A61B 17/7032 |
| | | | 606/278 |
| 2015/0025579 A1 * | 1/2015 | Biedermann | A61B 17/7011 |
| | | | 606/266 |
| 2015/0080960 A1 * | 3/2015 | Biedermann | A61B 17/7037 |
| | | | 606/278 |
| 2015/0088202 A1 * | 3/2015 | Charvet | A61B 17/7037 |
| | | | 606/265 |
| 2015/0134006 A1 * | 5/2015 | Ziolo | A61B 17/7037 |
| | | | 606/278 |
| 2015/0142059 A1 * | 5/2015 | Biedermann | A61B 17/7035 |
| | | | 606/266 |
| 2016/0262801 A1 * | 9/2016 | Rezach | A61B 17/7032 |
| 2017/0042584 A1 * | 2/2017 | Lehmann, Jr. | A61B 17/7037 |
| 2017/0086886 A1 * | 3/2017 | Duncan | A61B 17/7035 |
| 2017/0189074 A1 * | 7/2017 | Biedermann | A61B 17/7037 |

\* cited by examiner

ADAPTATION SPHERE SADDLE

FIELD OF INVENTION

This invention relates to surgical implantable instruments. Specifically, the invention relates to osteosurgical screw devices.

BACKGROUND OF INVENTION

Surgical implant systems have become ubiquitous in modern medicine. Surgical implantable instruments are used to strengthen, stabilize, and align anatomic structures. Spinal implants constitute about 40% of all orthopedic implants. Spinal implant systems are designed to apply and withstand relatively high mechanical forces so as to hold the spine in alignment while fusion takes place.

Pedicle screws are some of the most frequently implanted devices. During a spinal surgery, multiple pedicle screws can be screwed into bone tissue to provide anchor points for a rod having a predetermined shape configured to bring a patient's spine into a proper alignment. Most pedicle screws include two basic categories: rigid screws and polyaxial screws. In rigid screws, the head portion—the component securing the rod—is immobilized with respect to the screw. In polyaxial screws, the head portion can articulate with respect to the screw. Rigid screws have the advantage of being able to be manipulated, but lack the surgical intraoperative flexibility and ease of use that variable angle screws provide. A new category of polyaxial screws has been developed that allows the surgeon to transition a polyaxial screw from a variable angle configuration to a rigid configuration. These screws, however, lack the ability to be surgically manipulated in a sagittal direction.

During spinal deformity surgeries, it is often necessary to de-rotate the vertebral bodies to normalize the spine. Because patient anatomy varies, insertion of fixed angle surgical screws—in which the anchor segment is set at a fixed angle relative to the rod—can be difficult. Polyaxial and multi-axial screws, which allow the screw shank to pivot about the head portion, permit the screw to be tailored to a patient's unique anatomy before and during insertion of the rod.

This problem was first addressed by the device patented in the U.S. Pat. No. 8,277,490 (the '490 Patent), which is incorporated herein by reference in its entirety. The '490 Patent discloses a variable angle surgical screw permitting sequential tightening of the polyaxial rotational components of the head portion and selectively immobilizing the rod within the head portion. The surgical screw disclosed in the '490 Patent allows for correction of any deformity, including rotational, malalignment, longitudinal angulation, compression or distraction, or bust fracture deformities. The head portion described in the '490 Patent allows intraoperative manipulation of the vertebral bodies to create sagittal alignment as desired by the surgeon intraoperatively. This is the first pedicle screw in which the head portion has three-degrees of freedom in both rotation and translational motions.

The invention disclosed herein is a novel and non-obvious improvement of the polyaxial screw head disclosed in the '490 Patent.

SUMMARY OF THE INVENTION

In an embodiment, the invention comprises a tulip having a hollow tubular body. The tulip is configured to retain the head of a pedicle screw. The tulip has an aperture through which the screw shank protrudes. The screw shank is configured for insertion into a bone tissue. A rod locker is disposed within the tulip. Bevels are disposed on the tulip and the rod locker enabling sagittal and combined alignment of the rod.

The rod locker is transitionable between locked and unlocked configurations. In the unlocked configuration, a surgeon can change the orientation of the tulip with respect to the screw, whereas in the locked configuration, the rod locker immobilizes the tulip against articulation relative to the screw. A saddle is disposed within the rod locker. The saddle has a first concave surface configured to accept the rod and a second convex surface configured to facilitate adjustment of the rod alignment relative to the rod locker.

An outer set screw is disposed within the tulip. The outer set screw has an annular body with an inner lumen. The outer set screw is configured to retain the rod locker within the tulip. An inner set screw engages the inner lumen of the outer set screw. Positions of the inner and outer set screws within the tulip control ranges of motions of various components with respect to one another. Positions of the inner and outer set screws can be adjusted independently of one another.

The invention further includes a force distributor. The force distributor has a first concave surface configured to mate with a rod. The force distributor has a bore disposed therein. The bore is configured to accept the conical end of the inner set screw. The conical end of the inner set screw exerts a force onto the bore of the force distributor, and the force distributor is structured to distribute this force along the contact surface with the rod. The conical end of the inner set screw does not contact the rod directly and, instead, the force exerted by the conical end is distributed along the contact area between the rod and the force distributor. When the inner set screw is tightened, the force distributor immobilizes the rod within the saddle via frictional forces between the mated surface of the saddle and the rod.

In an embodiment, the outer set screw is in a screw-threaded engagement with the inner surface of the tulip, and the inner screw is in a screw-threaded engagement with the inner lumen of the outer screw. In an alternative embodiment, the inner and outer set screws may be retained in their position via complementary sets of ridges disposed on mated surfaces thereof. In this configuration, the inner and outer set screws can be snapped into their proper positions via application of a direct force rather than by being rotated along the direction of a thread.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The present invention provides a bone screw assembly in a spinal fixation system utilizing the pedicle of the spine. One skilled in the art will recognize that the invention is not limited to use in spinal surgery, and that the instrument and methods described herein can be adapted for use with any suitable surgical device and may be adapted for use in selected position in a variety of medical procedures. The present invention is described below using exemplary embodiments to provide an overall understanding of the principles of the structure, function, manufacture, and use of the instruments disclosed herein. Those skilled in the art will appreciate that the present invention may be implemented in a number of different applications and embodiments and is not specifically limited in its application to the particular embodiments depicted herein.

The exemplary surgical screw assemblies of the inventive embodiments may be used to engage one or more spinal fixation elements to bone. For example, a surgical screw assembly may be employed to fix a spinal plate, rod, and/or cable to a vertebra of the spine. Although the exemplary surgical screw assemblies described below are designed primarily for use in spinal applications, and specifically the pedicle region of a vertebra, one skilled in the art will appreciate that the structure, features and principles of the exemplary surgical screw assemblies, as well as the other exemplary embodiments described below, may be employed to couple any type of orthopedic implant to any type of bone or tissue. The surgical screw assembly facilitates correction of the position of a patient's vertebra in which the surgical screw is implanted.

Figure 1:
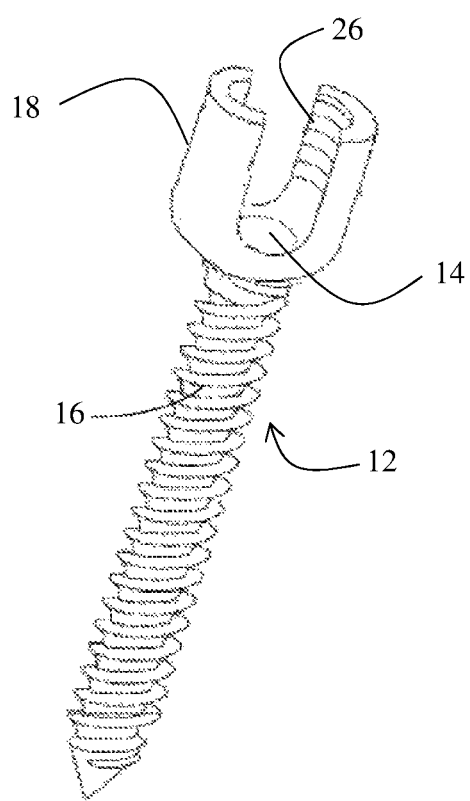
FIG. 1 is a perspective view depicting a pedicle screw within a tulip.

FIG. 1 depicts a screw 12 having a screw head 14 and screw shank 16. Screw head 14 resides within tulip 18. Tulip 18 contains an aperture through which screw shank 16 protrudes. Tulip 18 can be articulated about screw head 14 to achieve a desired angle between tulip 18 and screw shank 16. Screw shank 16 is configured to be screwed into patient's bone tissue.

Figure 2:
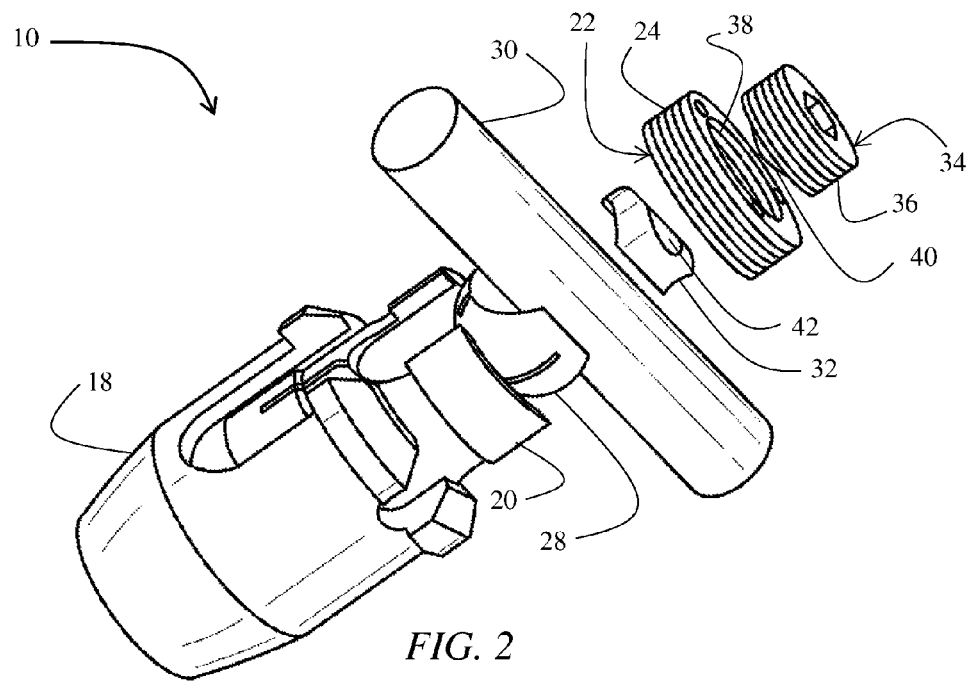
FIG. 2 is a perspective exploded view of the invention.

FIG. 2 depicts a head portion 10 of screw 12. A rod locker 20 is disposed within tulip 18. Distal surface of rod locker 20 engages screw head 14 within tulip 18. An annular outer set screw 22 has an outer male thread 24 configured to screw-threadedly engage female thread 26 disposed on an inner surface of tulip 18. When outer set screw 22 is screwed into tulip 18, the bottom surface of outer set screw 22 engages the top surface of rod locker 20. Outer set screw 22 urges rod locker 20 toward screw head 14 of screw 12. As outer set screw 22 is screwed into tulip 18, the magnitude of force applied by rod locker 20 onto screw head 14 increases. When set screw 22 is fully screwed into tulip 18, rod locker 20 immobilizes screw head 14 within tulip 18, thereby restricting tulip 18 from articulating relative to screw 12.

A saddle 28 is disposed within rod locker 20. Saddle 28 has a first concave surface configured to mate with an alignment rod 30. Saddle 28 has a second convex surface configured to facilitate articulation of rod 30 within U-shaped channels disposed within tulip 18 and rod locker 20. The U-shaped channels provide bevels that allow sagittal and combined rod alignment.

A force distributor 32 is positioned above rod 30. Force distributor 32 has a concave surface configured to accept rod 30. Force distributor 32 allows for the necessary pivot action of sagittal motion, as well as other degrees of freedom.

Figure 3:
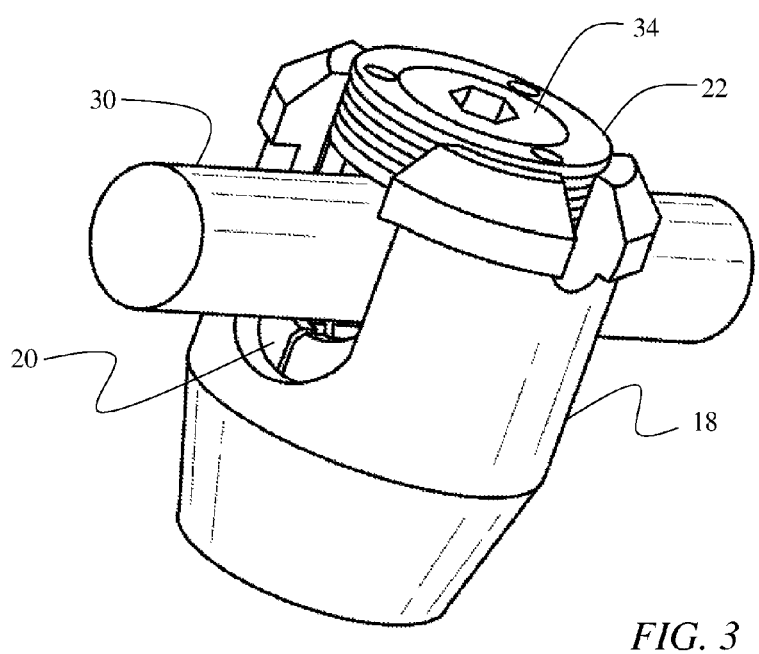
FIG. 3 is a perspective view of the invention in an assembled configuration.

An inner set screw 34 is disposed within a lumen of outer set screw 22. Inner set screw 34 has male thread 36 configured to screw-threadedly mate with female thread 38 disposed on the inner surface of outer set screw 22. Inner set screw 34 has a protruding conical end 40. Force distributor 32 includes a bore 42 configured to accept conical end 40 of set screw 34. Bore 42 can be a blind bore or a through bore. As inner set screw 34 is screwed into outer set screw 22, conical end 40 exerts a force onto bore 42. The force is distributed throughout the concave surface of force distributor 32 in contact with rod 30. Force distributor 32 provides an increased contact area with rod 30, thereby facilitating a more secure engagement and eliminating points of concentrated stress. In an embodiment, conical end 40 of inner set screw 34 does not directly contact rod 30 and, instead, the force exerted by conical end 40 is distributed along the contact area between rod 30 and force distributor 32. As inner set screw 34 is tightened within outer set screw 22, the magnitude of force exerted by force distributor 32 onto rod 30 increases, thus immobilizing rod 30 within saddle 28 as depicted in FIG. 3. In an embodiment, ends of force distributor 32 engage ends of saddle 28.

FIG. 3 illustrates head portion 10 in its assembled configuration. Outer set screw 22 can be tightened within tulip 18 independently of inner set screw 34. This allows the surgeon to first immobilize tulip 18 with respect to screw 12, then bring rod 30 into a proper alignment, and finally immobilize rod 30 by tightening inner set screw 34. This structural configuration facilitates surgical intraoperative flexibility and greatly increases the ease with which rod 30 may be properly aligned and immobilized.

While there has been described and illustrated specific embodiments of an intervertebral spacer device, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A surgical screw, comprising:
   a screw having a screw head and a screw shank, the screw shank configured for insertion into a bone tissue;
   a tulip having a hollow tubular body configured to retain the screw head, the tulip having an aperture through which the screw shank protrudes;
   a rod locker residing within the tulip, the rod locker having a locked and an unlocked configurations, wherein in the locked configuration, the rod locker immobilizes the tulip relative to the screw;
   a saddle having a first concave surface configured to accept the rod and a second convex surface configured to articulate within the tulip;
   an outer set screw having an annular body with an inner lumen, the outer screw configured to retain the rod locker within the tulip;
   an inner set screw engaging the inner lumen of the outer set screw, the inner set screw having a conical end;
   a force distributor having a concave surface configured to mate with a rod;
   a bore disposed within the force distributor, the bore accepting the conical end of the inner set screw, whereby the conical end exerts a force onto the bore of the force distributor, whereby the force distributor distributes the force along the concave surface in contact with the rod.

2. The surgical screw according to claim 1, wherein the outer set screw is in a screw-threaded engagement with the inner surface of the tulip.

3. The surgical screw according to claim 1, wherein the inner screw is in a screw-threaded engagement with the inner lumen of the outer screw.

4. The surgical screw according to claim 1, wherein the inner set screw is configured to immobilize the rod relative to the saddle.

5. The surgical screw according to claim 1, further comprising bevels disposed on the tulip and the rod locker enabling sagittal and combined alignment of the rod.

6. The surgical screw according to claim 1, further comprising a first plurality of ridges disposed on an inner surface of the tulip and a second plurality of ridges disposed on an outer surface of the outer set screw, wherein the first and the second plurality of ridges are configured to engage one another thereby retaining the outer set screw in a predetermined position relative to the tulip.

7. The surgical screw according to claim 1, further comprising a first plurality of ridges disposed on an inner lumen of the outer set screw and a second plurality of ridges disposed on an outer surface of the inner set screw, wherein the first and the second plurality of ridges are configured to engage one another thereby retaining the inner set screw in a predetermined position relative to the outer set screw.

8. The surgical screw according to claim 1, further comprising a female thread disposed on an inner lumen of the outer set screw and a male thread disposed on an outer lateral surface of the inner set screw, the male thread configured to mate with the female thread, whereby rotation of the inner set screw along a direction of the male thread increases a magnitude of force exerted by the conical end of the inner set screw onto the force distributor, thereby increasing a static friction between the force distributor and the rod.

9. A surgical screw, comprising:
- a screw having a screw head and a screw shank, the screw shank configured for insertion into a bone tissue;
- a tulip having a hollow tubular body configured to retain the screw head, the tulip having an aperture through which the screw shank protrudes;
- a rod locker residing within the tulip, the rod locker having a locked and unlocked configurations, wherein in the locked configuration, the rod locker immobilizes the tulip relative to the screw;
- an outer set screw having an annular body with an inner lumen, the outer screw configured to retain the rod locker within the tulip;
- a saddle disposed within the rod locker, the saddle having a first concave surface configured mate with a rod and a second convex surface configured to articulate within the tulip;
- an inner set screw engaging the inner lumen of the outer set screw, the inner set screw having a conical end;
- a force distributor disposed opposite the saddle, the force distributor having a concave surface configured to mate with the rod;
- a bore disposed within the force distributor, the bore accepting the conical end of the inner set screw, whereby the conical end exerts a force onto the bore of the force distributor, whereby the force distributor distributes the force along a contact area of the force distributor and the rod.

10. The surgical screw according to claim 9, wherein the outer set screw is in a screw-threaded engagement with the inner surface of the tulip.

11. The surgical screw according to claim 9, wherein the inner screw is in a screw-threaded engagement with the inner lumen of the outer screw.

12. The surgical screw according to claim 9, wherein the inner set screw is configured to immobilize the rod relative to the saddle.

13. The surgical screw according to claim 9, further comprising bevels disposed on the tulip and the rod locker enabling sagittal and combined alignment of the rod.

14. The surgical screw according to claim 9, further comprising a first plurality of ridges disposed on an inner surface of the tulip and a second plurality of ridges disposed on an outer surface of the outer set screw, wherein the first and the second plurality of ridges are configured to engage one another thereby retaining the outer set screw in a predetermined position relative to the tulip.

15. The surgical screw according to claim 9, further comprising a first plurality of ridges disposed on an inner lumen of the outer set screw and a second plurality of ridges disposed on an outer surface of the inner set screw, wherein the first and the second plurality of ridges are configured to engage one another thereby retaining the inner set screw in a predetermined position relative to the outer set screw.

16. The surgical screw according to claim 9, further comprising a female thread disposed on an inner lumen of the outer set screw and a male thread disposed on an outer lateral surface of the inner set screw, the male thread configured to mate with the female thread, whereby rotation of the inner set screw along a direction of the male thread increases a magnitude of force exerted by the conical end of the inner set screw onto the force distributor, thereby increasing a static friction between the force distributor and the rod.

\* \* \* \* \*